United States Patent
Stokbroekx et al.

(10) Patent No.: US 6,602,873 B2
(45) Date of Patent: Aug. 5, 2003

(54) ANGIOGENESIS INHIBITING THIADIAZOLYL PYRIDAZINE DERIVATIVES

(75) Inventors: Raymond Antoine Stokbroekx, Beerse (BE); Marc André Ceusters, Diest (BE); Marcel Jozef Maria Van der Aa, Turnhout (BE); Marcel Gerebernus Maria Luyckx, Geel (BE); Marc Willems, Vosselaar (BE); Robert W. Tuman, Chalfont, PA (US)

(73) Assignee: Janssen Pharamaceutica, N.V. (BE)

( * ) Notice: Subject to any disclaimer, the term of this patent is extended or adjusted under 35 U.S.C. 154(b) by 0 days.

(21) Appl. No.: 09/864,594

(22) Filed: May 24, 2001

(65) Prior Publication Data

US 2001/0046999 A1 Nov. 29, 2001

Related U.S. Application Data

(63) Continuation of application No. 09/446,495, filed as application No. PCT/EP98/04021 on Jun. 22, 1998, now Pat. No. 6,265,407.
(60) Provisional application No. 60/052,194, filed on Jul. 10, 1997.

(30) Foreign Application Priority Data

Jun. 24, 1997 (EP) .............................................. 97201930

(51) Int. Cl.[7] ..................... A61K 31/501; C07D 417/04
(52) U.S. Cl. .................................. 514/252.05; 544/238
(58) Field of Search ...................... 544/238; 514/252.05

(56) References Cited

U.S. PATENT DOCUMENTS

| | | | |
|---|---|---|---|
| 5,104,889 A | 4/1992 | Kanai et al. | |
| 5,610,166 A | 3/1997 | Singh | |
| 6,265,407 B1 | * 7/2001 | Stokbroekx et al. | ... 514/252.05 |

FOREIGN PATENT DOCUMENTS

| | | |
|---|---|---|
| EP | 0652000 B1 | 5/1995 |
| WO | WO 97/26258 A1 | 7/1997 |

OTHER PUBLICATIONS

Herbst et al. Semin. Oncol. Suppl.4,pp.66–77 (2002) (Abstract).*
Mitchell et al., Annual Reports In Medicinal Chemistry,27,p. 139–148, 1992.*
Folkman J., Tumor Angiogenesis: Therapeutic Implications. *N Engl J Med.* 1971 285:1182–1186.
Gimbrone M. A. Jr. et al., Tumor Dormancy In Vivo By Prevention Of Neovascularization. *J. Exp. Med.* 1972 136: 261–276.
Folkman J. et al., Angiogenesis Inhibition and Tumor Regression Caused by Heparin or a Heparin Fragment in the Presence of Cortisone. *Science* 1983 221: 719–725.
Folkman J. et al., Angiogenic Factors. *Science.* 1987 235:442–447.
Wolf J., Angiogenesis in Normal and Psoriatic Skin. *Laboratory Investigation* 1989 61: 139–142.
White, C. et al., Treatment of Pulmonary Hemangiomatosis With Recombinant Interferon: Alfa–2a. *N. Engl. J. Med.* 1989 320: 1197–1200.
Folkman, J., Successful Treatment of an Angiogenic Disease. *N. Engl. J. Med.* 1989 320: 1211–1212.
Kumar S. et al., Psoriasis, Angiogenesis and Hyaluronic Acid. *Laboratory Investigation* 1990 62: 664–665.
Folkman J., What is the evidence that tumors are angiogenesis dependent? *J Natl. Cancer Inst.* 1990: 83:4–6.
Auerbach R. et al. Assays for Angiogenesis. A Review. *Pharmac. Ther.* 1991 51: 1–11.
Moses M. et al., Inhibitors of Angiogenesis. *Bio/technology* 1991 9: 630–634.
Liotta L. et al., Cancer Metastasis and Angiogenesis: An Imbalance of Positive and Negative Regulation. *Cell* 1991 64: 327–336.

(List continued on next page.)

*Primary Examiner*—Emily Bernhardt
(74) *Attorney, Agent, or Firm*—Alana G. Kriegsman

(57) ABSTRACT

This invention concerns compounds of formula

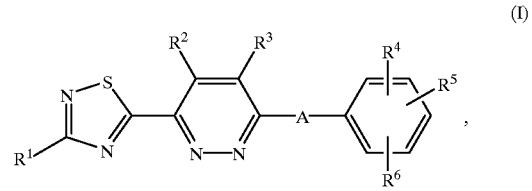

(I)

the N-oxide forms, the pharmaceutically acceptable acid addition salts and stereochemically isomeric forms thereof, wherein $R^1$ is hydrogen, $C_{1-6}$alkyl, $C_{1-6}$alkyloxy, $C_{1-6}$alkylthio, amino, mono- or di($C_{1-6}$alkyl)amino, $Ar^1$, $Ar^1$—NH—, $C_{3-6}$cycloalkyl, hydroxymethyl or benzyloxymethyl; $R^2$ and $R^3$ are hydrogen, or taken together may form a bivalent radical of formula —CH=CH—CH=CH—; $R^4$, $R^5$ and $R^6$ are each independently selected from hydrogen, halo, $C_{1-6}$alkyl, $C_{1-6}$alkyloxy, trifluoromethyl, nitro, amino, cyano, azido, $C_{1-6}$alkyloxy $C_{1-6}$alkyl, $C_{1-6}$alkylthio, $C_{1-6}$alkyloxycarbonyl or $Het^1$; or when $R^4$ and $R^5$ are adjacent to each other they may be taken together to form a radical of formula —CH=CH—CH=CH—; A is a bivalent radical of formula $NR^7$, $NR^7$-Alk$^1$-X-, $NR^7$-Alk$^1$-X-Alk$^2$-, O-Alk$^1$-X-, O-Alk$^1$-X-Alk$^2$- or S-Alk$^1$-X-; wherein X is a direct bond, —O—, —S—, C=O, —$NR^8$— or $Het^2$; $R^7$ is hydrogen, $C_{1-6}$alkyl or $Ar^2$methyl; $R^8$ is hydrogen, $C_{1-6}$alkyl or $Ar^2$methyl; Alk$^1$ is $C_{1-6}$alkanediyl; Alk$^2$ is $C_{1-4}$alkanediyl; $Ar^1$ and $Ar^2$ are optionally substituted phenyl; phenyl; $Het^1$ and $Het^2$ are optionally substituted heterocycles; having angiogenesis inhibiting activity; their preparation, compositions containing them and their use as a medicine.

10 Claims, No Drawings

OTHER PUBLICATIONS

Weidner N. et al., Tumor Angiogenesis and Metastasis—Correlation in Invasive Breast Carcinoma. *New Eng. J. Med.* 1991 324: 1–8.

Kusaka M. et al. Potent Anti–Angiogenic Action of AGM–1470: Comparison to the Fumagillin Parent. BBRC 1991 174: No. 3. 1070–1076.

Shweiki D. et al., Vascular Endothelial Growth Factor Induced by Hypoxia May Mediate Hypoxia–Initiated Angiogenesis. *Nature* 1992 359: 843–845.

Plate K. et al., Vascular Endothelial Growth Factor is a Potential Tumour Angiogenesis Factor in Human Gliomas In vivo. *Nature* 1992 359: 845–848.

Teicher B.A. et al., Antiangiogenic Agents Potentiate Cytotoxic Cancer Therapies Against Primary and Metastatic Disease. *Cancer Research* 1992 52: 6702–6704.

Kim K. et al., Inhibition of Vascular Endothelial Growth Factor–Induced Angiogenesis Suppresses Tumour Growth In Vivo. *Nature* 1993 362: 841–844.

Nabel E.G. et al., Recombinant Fibroblast Growth Factor–1 Promotes Intimal Hyperplasia And Angiogenesis In Arteries In Vivo, *Nature* 1993, 362: 844–845.

Aiello, L., et al., Vascular Endothelial Growth Factor in Ocular Fluid of Patients with Diabetic Retinopathy and Other Retinal Disorders. *New. Eng. J. Med.* 1994 331: 1480–1487.

Millauer B. et al., Glioblastoma Growth Inhibited in Vivo by a Dominant–Negative Flk–1 Mutant. *Nature* 1994 367: 576–579.

Fidler I. et al., The Implications of Angiogenesis for the Biology and Therapy of Cancer Metastasis. *Cell* 1994 79: 185–188.

O'Reilly M. et al., Angiostatin: A Novel Angiogenesis Inhibitor That Mediates the Suppression of Metastases by a Lewis Lung Carcinoma. *Cell* 1994 79: 315–328.

Watson S. et al., Inhibition of Organ Invasion by the Matrix Metalloproteinase Inhibitor Batimastat (BB–94) in Two Human Colon Carcinoma Metastasis Models. *Cancer Research* 1995 55: 3692–3633.

Singh R. et al., Interferons α and β Down–Regulate the Expression of Basic Fibroblast Growth Factor in Human Carcinomas. *Proc.Natl. Acad. Sci.* 1995 92: 4592–4566.

Folkman J., Clinical Applications of Research on Angiogenesis. *New Eng. J. Med.* 1995 333: 1757–1763.

Nissanov, J. et al. Methods in Laboratory Investigation: Automatic Vessel Segmentation and Quantification of the Rat Aortic Ring Assay of Angiogenesis *Lab. Investig.* 1995 73: 734–739.

Li V. W. et al., Cyclosporine and Angiogenesis in Psoriasis. *J. Am. Acad. Derm.* 1996 35(6):1019–1020.

Perez–Atayde A. et al., Spectrum of Tumor Angiogenesis in the Bone Marrow of Children with Acute Lymphoblastic Leukemia. *Am. J. Pathology* 1997 150:815–821.

O'Reilly M. et al., Endostatin: An Endogenous Inhibitor of Angiogenesis and Tumor Growth. *Cell* 1997 88: 277–285.

Lissbrant I. et al., Vascular Density Is a Predictor of Cancer–Specific Survival in Prostatic Carcinoma. *The Prostate* 1997 33: 38–45.

Nicosia R. F. et al. Endogneous Regulation of Angiogenesis in the Rat Aorta Model. *Am. J. Pathology* 1997 151 (5):1379–1386.

Kudelka A. et al. Complete Remission of Metastaic Cervical Cancer with the Angiogenesis Inhibitor TNP–470. *New Eng. J. Med.* 1998 338:991–992.

Brem S., Angiogenesis and Cancer Control: From Concept to Therapeutic Trial. Cancer Control, *Journal of the Moffit Cancer Center* 1999, vol. 6, No. 5, available at http://www.moffitt.usf.edu/pubs/ccj/v6n5/article2.htm.

Blackwell K. et al., Tamoxifen Inhibits Angiogenesis in Estrogen Receptor–Negative Animal Models. *Clin. Cancer Res.* 2000 6(11): 4359–4364 at 4359.

Clark F. et al., Ocular Angiostatic Agents, *Expert Opinion On Therapeutic Patents*, Ashley Publication Ltd., 2000, vol. 10(4): 427–448.

Kruger E. A. et al., Endostatin Inhibits Microvessel Formation in the Ex Vivo Rat Aortic Ring Angiogenesis Assay. BBRC 2000 268: 183–191.

Los M. et al., The Potential Role of Antivascular Therapy in the Adjuvant and Neoadjuvant Treatment of Cancer. *Semin Oncol* 2001 28:93–105 at 95.

Murray, Clifford J., Editor, Rat Aortic Ring. *Angiogenesis Protocols*, Human Press, Totowa, NJ 2001 Ch. 13, pp. 185–204, at 186.

Folkman J. et al., Angiogenesis Research: Guidelines For Translation To Clinical Application, *Thromb. Haemost.* 2001, 86: 23–33.

Nicosia et al., Growth of Microvessel in Serum–Free Matrix Culture of Rat Aorta, Laboratory Investigation, vol. 63, pp. 115–122, 1990.

Hungarian Search Report for Application No. P004457 dated Oct. 9, 2001.

PCT International Search Report No. WO9858929 (PCT/EP98/04021)dated Nov. 26, 1998 (attachment to Hungarian Search Report for Application No. P004457 dated Oct. 9, 2001).

Auerbach, et al; "Expression of Organ–Specific Antigens on Capillary Endothelial Cells"; Microvascular Research; 1985; pp. 401–411; vol. 29; Academic Press Inc.; USA.

Bogdanovic, S and Langlands, B.; "Angiogensis", Scrips Reports; Jun. 30, 2002; pp. 1–138; BS1185; PJB Publications Ltd., Surrey, UK.

Folkman, J.; "Tumor Angiogenesis"; Advances in Cancer Research; 1985; vol. 43; pp.175–203; Academie Press, Inc.

Kruger, et al.; "UCN–01, a Protein Kinase C Inhibitor, Inhibits Endothelial Cell Proliferation and Angiogenic Hypoxic Response", Invasion and Metastasis; 1988/99; pp. 209–218; vol. 18; S. Karger AG, Basel.

Liekens, et al; "The Sulfonic Acid Polymers PAMPS [Poly(2–Acrylamido–2–Methyl–1 Propanesulfonic Acid)] and Related Analogues Are Highly Potent Inhibitors of Angiogenesis", Oncology Research, 1997, pp. 173–178; vol. 9; Cognizant Comm. Corp; USA.

Patz, A.; "Clinical and Experimental Studies on Retinal Neovascularization"; American Journal of Opthalmology; Dec. 1982; pp. 715–743; vol. 94.

Singh, Jai P.; Pharmaceutical Compositions Against Angiogenesis and Angiogenic diseases Containing 2–Phenyl–3–Aroyl–Benzothiphene Derivatives and Process for Producing Them; Abstract of Hungarian Patent P9402955, equivalent of US Patent No. 5,610,166 and European Patent No. EP0652000 listed above.

* cited by examiner

ANGIOGENESIS INHIBITING THIADIAZOLYL PYRIDAZINE DERIVATIVES

CROSS REFERENCE TO RELATED APPLICATIONS

This application is a continuation of application Ser. No. 09/446,495, filed Aug. 14, 2000, now U.S. Pat. No. 6,265,407, which is the national stage of application Ser. No. PCT/EP98/04021, filed Jun. 22, 1998 which application claims priority from EP 97201930.1, filed Jun. 24, 1997 and U.S. Provisional Application No. 60/052,194, filed Jul. 10, 1997.

This invention concerns novel 3-(3-substituted-1,2,4-thiadiazol-5-yl)pyridazine derivatives acting as angiogenesis inhibitors, and their preparation; it further relates to compositions comprising them, as well as their use as a medicine.

Angiogenesis, i.e. the formation of new vessels by endothelial cells, plays an important role in a variety of physiologic and pathophysiologic processes. The development of a vascular supply is essential for the growth, maturation and maintenance of normal tissues. It is also required for wound healing. Angiogenesis is critical for solid tumor growth and metastasis and is involved in a variety of other pathological conditions such as neovascular glaucoma, diabetic retinopathy, psoriasis and rheumatoid arthritis. These pathological states are characterized by augmented angiogenesis during which normally quiescent endothelial cells become activated, degrade extracellular matrix barriers, proliferate, and migrate to form new vessels. To control these angiogenesis dependent disorders, compounds with angiogenesis inhibitory properties would be very useful.

Several compounds inhibiting angiogenesis, also called angiostatics, angio-inhibitors or angiogenic antagonists, are disclosed in the art. For instance hydrocortisone is a well known angiogenesis inhibitor (Folkman et al., Science 230:1375, 1985'"A new class of steroids inhibits angiogenesis in the presence of heparin or a heparin fragment"; Folkman et al., Science 221:719, 1983, "Angiogenesis inhibition and tumor regression caused by heparin or a heparin fragment in the presence of cortisone").

EP-0,398,427, publised on Nov. 22, 1990, discloses anti-rhinoviral pyridazinames, and in EP-0,435,381, published on Jul. 3, 1991, pyridazinamines are described having anti-picornaviral activity. EP-0,429,344, published on May 29, 1991, discloses aminopyridazine derivatives as cholinergic agonists.

The compounds of the present invention differ from the prior art compounds by the fact that they are invariably substituted with a thiadiazolyl moiety and particularly by the fact that unexpectedly these compounds have angiogenesis inhibiting properties.

This invention concerns compounds of formula

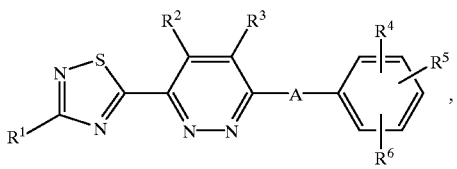

(I)

the N-oxide forms, the pharmaceutically acceptable acid addition salts and stereochemically isomeric forms thereof, wherein $R^1$ is hydrogen, $C_{1-6}$alkyl, $C_{1-6}$alkyloxy, $C_{1-6}$alkylthio, amino, mono- or di($C_{1-6}$alkyl)amino, $Ar^1$, $Ar^1$—NH—, $C_{3-6}$cycloalkyl, hydroxymethyl or benzyloxymethyl;

$R^2$ and $R^3$ are hydrogen, or taken together may form a bivalent radical of formula —CH=CH—CH=CH—;

$R^4$, $R^5$ and $R^6$ are each independently selected from hydrogen, halo, $C_{1-6}$alkyl, $C_{1-6}$alkyloxy, trifluoromethyl, nitro, amino, cyano, azido, $C_{1-6}$alkyloxy$C_{1-6}$alkyl, $C_{1-6}$alkylthio, $C_{1-6}$alkyloxycarbonyl or $Het^1$;

or when $R^4$ and $R^5$ are adjacent to each other they may be taken together to form a radical of formula —CH=CH—CH=CH—;

A is a bivalent radical of formula

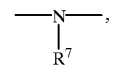 (a-1)

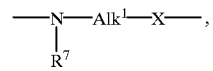 (a-2)

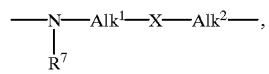 (a-3)

 (a-4)

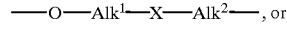 (a-5), or

 (a-6)

wherein X is a direct bond, —O—, —S—, C=O, —NR$^8$— or Het$^2$;

$R^7$ is hydrogen, $C_{1-6}$alkyl or Ar$^2$methyl;
$R^8$ is hydrogen, $C_{1-6}$alkyl or Ar$^2$methyl;
Alk$^1$ is $C_{1-6}$alkanediyl;
Alk$^2$ is $C_{1-4}$alkanediyl;
Ar$^1$ is phenyl; phenyl substituted with 1, 2 or 3 substituents each independently selected from halo, $C_{1-6}$alkyl, $C_{1-6}$alkyloxy, trihalomethyl, amino or nitro;
Ar$^2$ is phenyl; phenyl substituted with 1, 2 or 3 substituents each independently selected from halo, $C_{1-6}$alkyl, $C_{1-6}$alkyloxy, trihalomethyl, amino or nitro;
Het$^1$ is a monocyclic heterocycle selected from oxazolyl, isoxazolyl, oxadiazolyl, thiazolyl, isothiazolyl, thiadiazolyl or oxazolinyl; and each monocyclic heterocycle may optionally be substituted on a carbon atom with $C_{1-4}$alkyl; and
Het$^2$ is tetrahydrofuran; a tetrahydrofuran substituted with $C_{1-6}$alkyl; a dioxane; a dioxane substituted with $C_{1-6}$alkyl; a dioxolane; or a dioxolane substituted with $C_{1-6}$alkyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; $C_{1-6}$alkyl is meant to include $C_{1-4}$alkyl and the higher homologues thereof having 5 to 6 carbon atoms such as, for example, pentyl, 2-methylbutyl, hexyl, 2-methylpentyl and the like; $C_{2-4}$alkanediyl defines bivalent straight and branched chain saturated hydrocarbon radicals having from 2 to 4 carbon atoms such as, for example, 1,2-ethanediyl, 1,3-propanediyl, 1,4-butanediyl and the like; $C_{1-4}$alkanediyl is meant to include $C_{2-4}$alkanediyl and methylene; and $C_{1-6}$alkanediyl is meant to include $C_{1-4}$alkanediyl and the higher homologues thereof having 5 to 6 carbon atoms such as, for example, 1,5- pentanediyl, 1,6-hexanediyl and the like. The term "C=O" refers to a carbonyl group.

Wherever in the compounds of the present invention the bivalent radical A is (a-2) or (a-3), the nitrogen of the —NR⁷— moiety is preferably linked to the pyridazinyl moiety of said compound. Analogously, wherever the bivalent radical A is (a-4), (a-5) or (a-6) the oxygen or sulfur atom is preferably linked to the pyridazinyl moiety. Examples of the bivalent radical A are for instance,

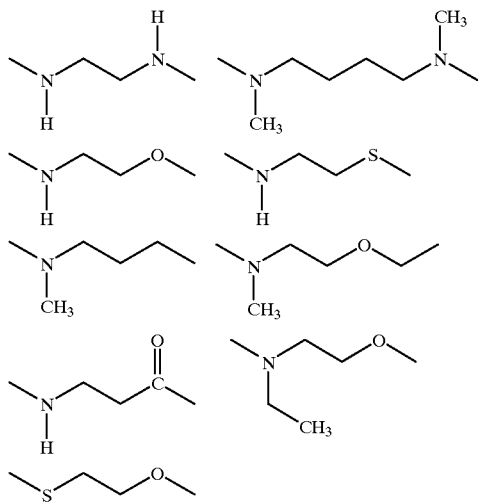

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one of the pyridazinyl nitrogens is N-oxidized.

Whenever used hereinafter, the term "compounds of formula (I)" is meant to include also the pharmaceutically acceptable acid addition salts and all stereoisomeric forms.

A group of interesting compounds consists of those compounds of formula (I) wherein one or more of the following restrictions apply:

a) $R^1$ is hydrogen, $C_{1-6}$alkyl, amino or di($C_{1-6}$alkyl)amino;

b) $R^2$ and $R^3$ are hydrogen;

c) $R^4$, $R^5$ and $R^6$ are each independently selected from hydrogen, halo, $C_{1-6}$alkyl, $C_{1-6}$alkyloxy, trifluoromethyl, nitro, $C_{1-6}$alkyloxycarbonyl or Het¹;

d) the bivalent radical A is (a-2) or (a-3) wherein $R^7$ is hydrogen or $C_{1-6}$alkyl, or A is (a-6) wherein X is O; Alk¹ in said radicals (a-2), (a-3) or (a-6) is preferably $C_{2-4}$alkanediyl.

A particular group of compounds are those compounds of formula (I) wherein $R^1$ is hydrogen, $C_{1-4}$alkyl or di($C_{1-4}$alkyl)amino; $R^2$ and $R^3$ are hydrogen; $R^4$, $R^5$ and $R^6$ are each independently selected from hydrogen, halo, $C_{1-4}$alkyl, $C_{1-4}$alkyloxy, trifluoromethyl, nitro, $C_{1-4}$alkyloxycarbonyl or Het¹; and the bivalent radical A is (a-2), (a-3), (a-4) or (a-6) wherein Alk¹ is preferably $C_{2-4}$alkanediyl.

A preferred group of compounds are those compounds of formula (I) wherein the bivalent radical A is (a-2), (a-4), or (a-6) wherein Alk¹ is $C_{2-4}$alkanediyl.

A more preferred group of compounds are those preferred compounds wherein Alk¹ is butanediyl.

Most preferred are:

6-(3-methyl-1,2,4-thiadiazol-5-yl)-N-[4-[3-(trifluoromethyl)phenoxy]butyl]-3-pyridazinamine N-methyl-6-(3-methyl-1,2,4-thiadiazol-5-yl)-N-[4-[3-(trifluoromethyl)phenoxy]butyl]-3-pyridazinamine, and 6-(3-methyl-1,2,4-thiadiazol-5-yl)-N-[4-[3-(trifluoromethyl)phenylthio]butyl]-3-pyridazinamine, and the pharmaceutically acceptable acid addition salts, the stereoisomeric forms, or the N-oxides thereof.

The compounds of the present invention can generally be prepared by reacting a pyridazine of formula (II) with an intermediate of formula (III).

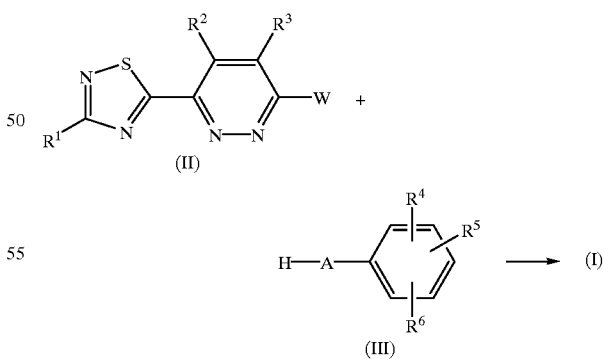

In the foregoing and following reaction schemes W represents an appropriate reactive leaving group such as, for example, halo, e.g. fluoro, chloro, bromo, iodo, or in some instances W may also be a sulfonyloxy group, e.g. methanesulfonyloxy, benzene-sulfonyloxy, trifluoromethanesulfonyloxy and the like reactive leaving groups. Said reaction is performed following art-known procedures such as for instance stirring both reactants together in a reaction-inert solvent, e.g. N,N-dimethylformamide, acetonitrile, methyl isobutylketone and the like, preferably in the presence of a base, e.g. sodium hydrogen carbonate, sodiumcarbonate or triethylamine. The reaction may conveniently be carried out at a temperature ranging between room temperature and the reflux temperature of the reaction mixture.

The compounds of formula (I) wherein the bivalent radical A' is a radical of formula (a-2), (a-4) or (a-6) wherein X is a direct bond, said compounds being represented by formula (I-a), can be prepared by condensing a phenol of formula (V) and an intermediate of formula (IV), e.g. by using the Mitsunobu reaction (Synthesis, 1, 1981). Said reaction is carried out in a reaction-inert solvent such as, e.g. THF, and in the presence of triphenylphosphine and diisopropryl azodicarboxylate (DIAD).

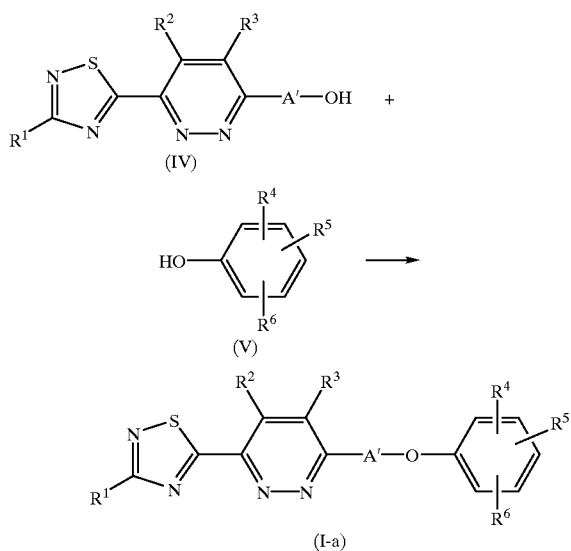

Further, the compounds of formula (I-a) can also be prepared following art-known O-alkylation reactions by reacting an intermediate of formula (VI), wherein W is a leaving group as defined above, with a phenol of formula (V) wherein A' is as defined above.

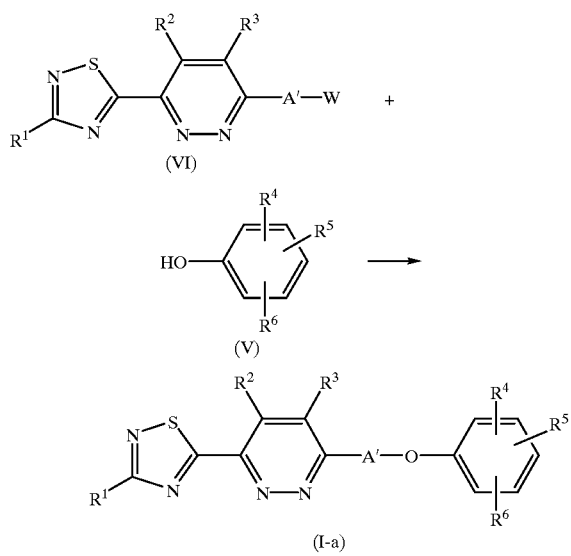

Said O-alkylation reaction can conveniently be carried out by mixing the reactants, optionally in a reaction-inert solvent. The addition of an appropriate base such as, e.g. sodium carbonate, sodium hydrogen carbonate, sodium hydroxide and the like, may optionally be used to pick up the acid which is formed during the course of the reaction. Further, it may be advantageous to convert the phenol of formula (V) first into a suitable salt form thereof such as, for example, an alkali or earth alkaline metal salt, by reacting (V) with an appropriate base as defined hereinabove and subsequently using said salt form in the reaction with the intermediate of formula (VI). Stirring and somewhat elevated temperatures may enhance the rate of the reaction; more in particular the reaction may be conducted at the reflux temperature of the reaction mixture. Additionally, it may be advantageous to conduct said alkylation reaction under an inert atmosphere such as, for example, oxygen-free argon or nitrogen gas.

The compounds of formula (I) may further be prepared by converting compounds of formula (I) into each other according to art-known group transformation reactions. For instance, compounds of formula (I) wherein the bivalent radical A is a radical of formula (a-2) to (a-6) wherein X is Het$^2$ and said Het$^2$ is a dioxane can be converted to the corresponding compounds of formula (I) wherein said X is C=O by hydrolysis under acidic conditions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art.

Intermediates of formula (II) may be prepared by reacting compounds of formula (VII), wherein W is an appropriate leaving group as defined above, with an intermediate of formula (VIII), optionally added as its acid addition salt.

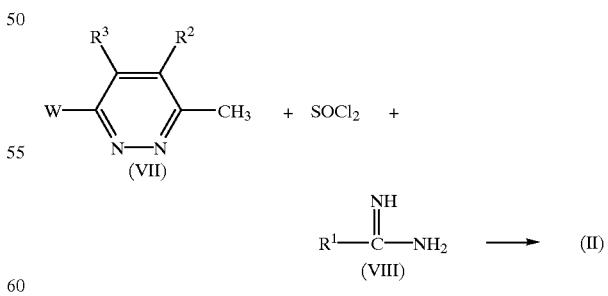

Intermediates of formula (III) wherein the bivalent radical A represents a radical of formula (a-2), said intermediates represented by intermediates (III-a), or wherein said radical A represents a radical of formula (a-3), said intermediates represented by intermediates (III-b), can be prepared by reacting their corresponding halo analogues, i.e. intermediates (IX) or (X), with an intermediate of formula (XI).

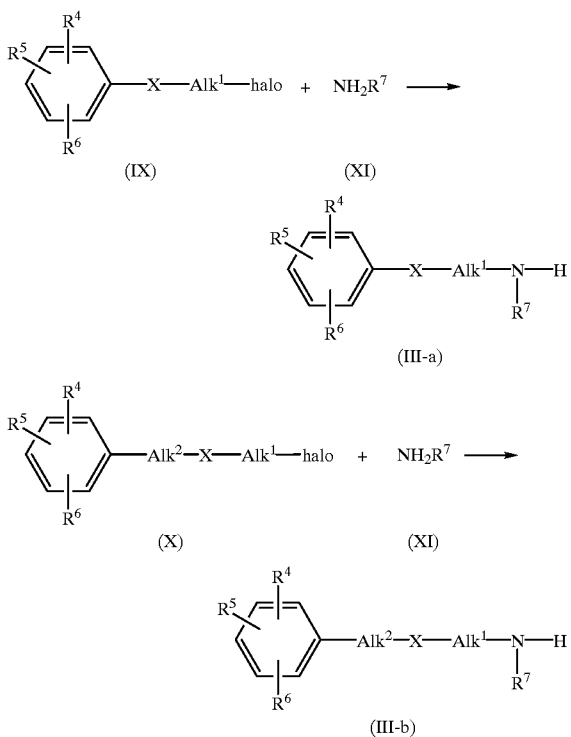

Said reaction can be carried out by stirring an intermediate of formula (IX) or (X) with an intermediate of formula (XI) in a reaction-inert solvent such as, e.g. THF, in the presence of calciumoxide. Optionally, the temperature may be raised in a range between room temperature and the reflux temperature of the reaction mixture and, if desired, the reaction may be carried out in an autoclave at an increased pressure.

The intermediates of formula (IX) or (X) can also be reacted with an intermediate of formula (XI) wherein one of the hydrogen atoms on the nitrogen is replaced by an appropriate protecting group, such as, e.g. a benzyl group. If desired art-known functional group transformations may be carried out before said protecting group is removed using art-known procedures such as, e.g. hydrogenation with palladium on carbon in the presence of hydrogen gas.

Intermediates of formula (IV), wherein A' represents a bivalent radical of formula (a-2), (a-4) or (a-6) wherein X is O, can be prepared by reacting an intermediate of formula (II) with an intermediate of formula (XII) in a reaction-inert solvent such as, e.g. N,N-dimethylformamnide, and optionally in the presence of a suitable base such as, e.g. sodium carbonate.

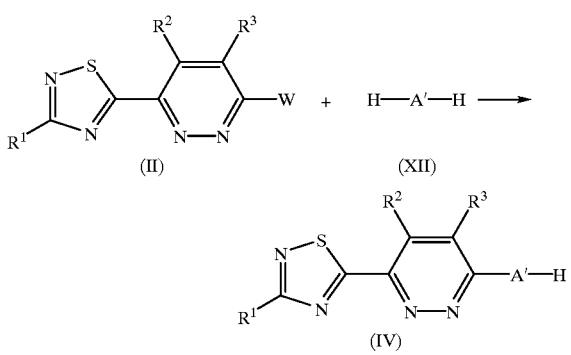

Compounds of formula (I) and some of the intermediates may have one or more stereogenic centers in their structure, present in a R or a S configuration. For instance, compounds of formula (I) wherein the bivalent radical A is a radical of formula (a-2) to (a-6) wherein $Alk^1$ is $C_{2-6}$alkanediyl can have a stereogenic center such as, e.g. compounds 88 and 89.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Suitable chiral stationary phases are, for example, polysaccharides, in particular cellulose or amylose derivatives. Commercially available polysaccharide based chiral stationary phases are ChiralCel CA, OA, OB, OC, OD, OF, OG, OJ and OK, and Chiralpak AD, AS, OP(+) and OT(+). Appropriate eluents or mobile phases for use in combination with said polysaccharide chiral stationary phases are hexane and the like, modified with an alcohol such as ethanol, isopropanol and the like. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) have valuable pharmacological properties in that they inhibit angiogenesis, both in vivo and in vitro, as demonstrated in the pharmacological example C.1.

In view of their pharmacological activity, the compounds of formula (I), their pharmaceutically acceptable acid addition salts, stereochemically isomeric forms, or N-oxide forms thereof, are inhibitors of angiogenesis. Therefore, angiogenesis inhibitors are useful to control or treat angiogenesis dependent disorders such as, e.g. ocular neovascular diseases, neovascular glaucoma, diabetic retinopathy, retrolental fibroplasia, hemangiomas, angiofibromas, psoriasis, osteoarthritis and rheumatoid arthritis. Also, angiogenesis inhibitors are useful to control solid tumor growth, such as, e.g. breast, prostate, melanoma, renal, colon, cervical cancer and the like; and metastasis.

Hence, the present invention discloses the compounds of formula (I) for use as a medicine as well as the use of these compounds of formula (I) for the manufacture of a medicament for treating angiogenesis dependent disorders.

In view of the usefulness of the subject compounds in the treatment or prevention of angiogenesis dependent disorders, the present invention provides a method of treating warm-blooded animals suffering from such disorders, said method comprising the systemic administration of a therapeutic effective amount of a compound of formula (I), a N-oxide or a pharmaceutically acceptable acid addition salt thereof.

In view of their useful pharmacological properties, the subject compounds may be formulated into various pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxy-propyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerin.

For intranasal administration the compounds of the invention may be used, for example, as a liquid spray, as a powder or in the form of drops.

Those skilled in the art could easily determine the effective amount from the test results presented hereinafter. In general it is contemplated that an effective amount would be from 0.001 mg/kg to 10 mg/kg body weight, and in particular from 0.01 mg/kg to 1 mg/kg body weight. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

The following examples are provided for purposes of illustration.

Experimental part

Hereinafter "DMF" means N,N-dimethylformamide, "DCM" means dichloromethane, "DIPE" means diisopropylether and "THFI" means tetrahydrofuran.

A. Preparation of the Intermediates

EXAMPLE A.1

3-Chloro-6-methylpyridazine (0.3 mol) and thionyl chloride (400 g) were stirred and refluxed overnight. The solvent was evaporated. The residue was taken up in DCM (500 ml). The mixture was cooled to 0° C. 1-Imino-ethanamine hydrochloride (1:1) (33 g) was added. Then sodium hydroxide (50%, 80 ml) was added dropwise at 0° C. The mixture was allowed to warn to room temperature, then stirred for 1 hour, poured out into ice water, stirred for 30 minutes and filtered over dicalite. The organic layer was separated, dried, filtered and the solvent was evaporated. The residue was boiled in ethanol (800 ml), silica gel (20 g) and activated charcoal Norit (3 g). The mixture was filtered over dicalite and the filtrate was evaporated. The residue was purified over silica gel on a glass filter (eluent:DCM). The pure fractions were collected and the solvent was evaporated. The residue was crystallized from ethanol. The precipitate was filtered off and dried, yielding: 18.3 g (29%) 3-chloro-6-(3-methyl-1,2,4-thiadiazol-5-yl)pyridazine (intermediate 1).

In a similar way, 3-chloro-6-(1,2,4-thiadiazol-5-yl)pyridazine (intermediate 2) and 5-(6-chloro-3-pyridazinyl)-N,N-dimethyl-1,2,4-thiadiazol-3-amine (intermediate 3) were prepared.

EXAMPLE A.2

A mixture of 4-(4-bromobutoxy)- 1,2-dichlorobenzene (0.03 mol), methylamine (20 g) and calciumoxide (7 g) in THF (100 ml) was stirred at 125° C. overnight in an autoclave. The mixture was filtered over dicalite and the filtrate was evaporated. The residue was taken up in DIPE and the mixture was filtered over dicalite. The filtrate was converted into the hydrochloric acid salt (1:1) with HCl/2-propanol. The precipitate was filtered off and dried, yielding 6 g (70.3%) of 4-(3,4-dichlorophenoxy)-N-methyl-1-butanamine (intermediate 4, mp. 132° C.).

EXAMPLE A.3

A mixture of 1-bromo-3-(trifluoromethyl)benzene (0.1 mol), 1,6-hexanediamine (0.5 mol) and copper(I)oxide (1 g) was stirred for 5 hours at 140° C. and left standing overnight. Water was added and the mixture was extracted with DCM. The organic layer was dried, filtered off and evaporated. The residue was purified on a glass filter over silica gel (eluent: $CH_2Cl_2/CH_3OH$ 98/2 to 90/10). The pure fractions were collected and evaporated. The oily residue was dissolved in DIPE and converted into the hydrochloric acid salt (1:2) in 2-propanol The precipitate was filtered off and dried, yielding 10 g (30%) of N-[3-(trifluoromethyl)phenyl]-1,6-hexanediamine dihydro-chloride (intermediate 5).

In a similar way, N-phenyl-1,4-butanediamine dihydro-chloride (intermediate 6) was prepared.

EXAMPLE A.4 a) A mixture of 1-(4-bromobutoxy)-3-(trifluoromethyl)-benzene (0.11 mol) and benzylamine (0.6 mol) in dimethylacetamide (250 ml) was stirred at 80° C for 6 hours, then poured out into water and extracted with toluene. The organic layer was separated, dried, filtered and the solvent was evaporated. The residue was converted into the hydrochloric acid salt (1:1) from DIPE. The precipitate was filtered off and dried. The residue was stirred in water. The precipitate was filtered off and dried, yielding 23.3 g (59%) of N-[4-[3-(trifluoromethyl)phenoxy]butyl]benzenemethaneamine hydrochloride (intermediate 7).

b) A mixture of intermediate 7 (0.03 mol) and paraformaldehyde (2 g) in methanol (150 ml) was hydrogenated with palladium on carbon (2 g) as a catalyst in the presence of thiophene (4%, 2 ml) and potassium acetate (4 g). After uptake of hydrogen gas (1 equivalent), the catalyst was filtered off and the filtrate was evaporated. The residue was stirred in water and this mixture was extracted with DCM. The separated organic layer was dried, filtered, and the solvent evaporated. The residue was dissolved in DIPE and converted into the hydrochloric acid salt (1:1) with HCl/2-propanol. The precipitate was filtered off and dried, yielding 8.22 g (73%) of N-methyl-N-[4-[3-(trifluoro-methyl)phenoxy]butyl]benzenemethanamine hydrochloride (intermediate 8).

c) A mixture of intermediate 8 (0.019 mol) in methanol (150 ml) was hydrogenated with palladium on carbon (10%, 2 g) as a catalyst. After uptake of hydrogen gas (1 equivalent), the catalyst was filtered off and the filtrate was evaporated. The residue was converted into the free base with a NaOH solution. The aqueous solution was extracted with toluene. The organic layer was separated, dried, filtered and the solvent was evaporated. The residue was converted into the hydrochloric acid salt (1:1) in DIPE. The precipitate was filtered off and dried, yielding 1.21 g (22.5%) of N-methyl-4-[3-(trifluoromethyl)phenoxy]-1-butanamine (intermediate 9).

EXAMPLE A.5

A mixture of intermediate 1 (0.08 mol), 4-methylamino-1-butanol (0.11 mol) and sodium carbonate (10 g) in DMF (150 ml) was stirred at 60° C. for 4 hours. The solvent was evaporated. The residue was taken up in DCM. The mixture was stirred, filtered over dicalite and the filtrate was evaporated. The residue was purified over silica gel on a glass filter (eluent: $CH_2Cl_2/CH_3OH$ 100/0 to 97/3). The pure fractions were collected and the solvent was evaporated, yielding 22.2 g (100%) of 4-[methyl[6-(3-methyl-1,2,4-thiadiazol-5-yl)-3-pyridazinyl]amino]-1-butanol (intermediate 10).

B. Preparation of the Final Compounds

EXAMPLE B.1

A mixture of intermediate 1 (0.02 mol), intermediate 9 (0.0212 mol) and sodium carbonate (0.03 mol) in DMF (60 ml) was stirred and heated at 60° C. overnight. The mixture was evaporated, the residue was dissolved in a mixture of toluene and water and separated into its layers. The aqueous layer was extracted with toluene. The combined organic layer was dried, filtered and the solvent was evaporated. The residue was purified over silica gel on a glass filter (eluent:DCM). The pure fractions were collected and the solvent was evaporated. The residue was crystallized from 2-propanol. The precipitate was filtered off and dried, yielding 2.77 g (33%) of N-methyl-6-(3-methyl- 1,2,4-thiadiazol-5-yl)-N-[4-[3-(trifluoromethyl)phenoxy]butyl]-3-pyridazinamine (compound 52).

EXAMPLE B.2

Diisopropryl azodicarboxylate (DIAD) (0.016 mol) in a small amount of THF was added dropwise to a mixture of intermediate 10 (0.008 mol), 4-trifluoromethyl-phenol (0.01 mol) and triphenylphosphine (0.016 mol) in THF (60 ml)

while cooling on ice. The mixture was stirred at room temperature for 30 minutes. The solvent was evaporated. The residue was purified over silica gel on a glass filter (eluent:DCM). The pure fractions were collected and the solvent was evaporated. The residue was dissolved in DIPE and converted into the hydrochloric acid salt (1:1). The precipitate was filtered off and dried. This fraction was boiled in DIPE, filtered off and dried, yielding 1.31 g (36%) of N-methyl-6-(3-methyl-1,2,4-thiadiazol-5-yl)-N-[4-[4-(tri-fluoromethyl)phenoxy]butyl]-3-pyridazinamine monohydrochloride (compound 55).

EXAMPLE B.3

A mixture of compound (95) (0.0065 mol) in an aqueous solution of sulfuric acid (1%, 200 ml) was stirred and refluxed overnight. The reaction mixture was cooled and the precipitate was filtered off, washed with water and dried, yielding 3 g (100%) of 5-[[6-(3-methyl-1,2,4-thiadiazol-5-yl)-3-pyridazinyl]amino]-1-[3-(trifluoromethyl)-phenyl]-1-pentanone (compound 69).

EXAMPLE B.4 a) A mixture of 3-chloro-6-cyano-pyridazine (0.03 mol) in triethylamine (12 ml) and DMF (50 ml) was stirred on an ice bath. Hydrogen sulfide was bubbled through the mixture for 20 minutes. The mixture was stirred overnight. Nitrogen gas was bubbled through the mixture for 1 hour. The mixture was poured out into water. The precipitate was filtered off, washed with water, dissolved in DMF and the solvent was evaporated, yielding 3 g (48%) of 6-mercapto-3-pyridazinecarbothioamide (intermediate 11).

b) A mixture of intermediate 11 (0.017 mol) in DMF (80 ml) was stirred at room temperature. Sodium hydride (50%, 0.02 mol) was added portionwise. The mixture was stirred for 30 minutes. A mixture of 1-(4-chlorobutoxy)-3-(trifluoromethyl)-benzene (0.02 mol) in DMF (20 ml) was added dropwise. The mixture was stirred at room temperature overnight. The solvent was evaporated. The residue was stirred in DIPE (100 ml), filtered off and dried, yielding 3.1 g (47%) of 6-[[4-[3-(trifluoromethyl)-phenoxy]butyl]thio]-3-pyridazinecarbothioamide (intermediate 12).

c) A mixture of intermediate 12 (0.009 mol) and N,N-dimethylacetamide dimethyl acetal (0.015 mol) in toluene (100 ml) was stirred and refluxed for 3 hours. The solvent was evaporated, yielding 4.1 g (100%) of N-[1-(dimethylamino)ethylidene]-6-[[4-[3-(trifluoromethyl)phenoxy]butyl]thio]-3-pyridazinecarbothioamide (intermediate 13).

d) A mixture of intermediate 13 (0.009 mol) and pyridine (0.02 mol) in ethanol (80 ml) was stirred. A mixture of hydroxylamine-O-sulfonic acid (0.01 mol) in methanol (20 ml) was added. The mixture was stirred overnight. The solvent was evaporated. The residue was taken up in DCM. The organic solution was washed with a diluted NaOH solution and with water, dried, filtered and the solvent was evaporated. The residue was purified by column chromatography over silica gel (eluent:DCM). The pure fractions were collected and the solvent was evaporated. The residue was crystallized from 2-propanol. The precipitate was filtered off and dried, yielding 1 g (26%) of 3-(3-methyl-1,2,4-thiadiazol-5-yl)-6-[[4-[3-(trifluoromethyl)phenoxy]butyl]thio]pyridazine (compound 94).

EXAMPLE B.5

A mixture of compound (101) (0.0094 mol) in HCl(80 ml) was stirred and refluxed for 25 minutes. The mixture was cooled on ice, alkalized with a concentrated $NH_4OH$ solution and extracted with DCM. The organic layer was separated, dried, filtered and the solvent was evaporated. The residue was purified over silica gel on a glass filter (eluent: $CH_2Cl_2/CH_3OH$). The pure fractions were collected and the solvent was evaporated. The residue was dissolved in 2-propanol and converted into the hydrochloric acid salt with HCl/2-propanol. The mixture was allowed to crystallize out. The precipitate was filtered of and dried, yielding 1.1 g (2%) of compound (102).

Tables F.1 to F.5 list the compounds that were prepared according to one of the above examples and table F.6 lists both the experimental (column heading "exp.") and theoretical (column heading "theor.") elemental analysis values for carbon, hydrogen and nitrogen of the compounds as prepared in the experimental part hereinabove.

TABLE F.1

| Co. No. | Ex. No. | $R^1$ | $R^4$ | $R^7$ | $R^8$ | $Alk^1$ | Physical data |
|---|---|---|---|---|---|---|---|
| 1 | B.1 | $CH_3$ | H | H | H | $-(CH_2)_2-$ | mp. 148.4° C. |
| 2 | B.1 | $CH_3$ | H | H | H | $-(CH_2)_3-$ | mp. 162.7° C. |
| 3 | B.1 | $CH_3$ | H | H | H | $-(CH_2)_4-$ | — |
| 4 | B.1 | $CH_3$ | H | H | H | $-(CH_2)_5-$ | mp. 139.9° C. |
| 5 | B.1 | $CH_3$ | H | H | H | $-(CH_2)_6-$ | mp. 135.1° C. |
| 6 | B.1 | $CH_3$ | 3-$CF_3$ | H | H | $-(CH_2)_2-$ | — |
| 7 | B.1 | $CH_3$ | 3-$CF_3$ | H | H | $-(CH_2)_3-$ | — |
| 8 | B.1 | $CH_3$ | 3-$CF_3$ | H | H | $-(CH_2)_6-$ | mp. 121.9° C. |
| 9 | B.1 | $CH_3$ | H | $CH_3$ | H | $-(CH_2)_2-$ | mp. 127.9° C. |
| 10 | B.1 | $CH_3$ | H | $CH_3$ | $CH_3$ | $-(CH_2)_2-$ | mp. 126.2° C. |
| 97 | B.1 | $(CH_3)_2N-$ | 3-$CF_3$ | H | H | $-(CH_2)_6-$ | HCl (1:2) |
| 104 | B.1 | $CH_3$ | 3-$CF_3$ | $CH_3$ | H | $-(CH_2)_3-$ | — |
| 105 | B.1 | $CH_3$ | 3-$CF_3$ | H | $CH_3$ | $-(CH_2)_2-$ | — |
| 106 | B.1 | $CH_3$ | 3-$CF_3$ | H | $CH_3$ | $-(CH_2)_4-$ | — |
| 107 | B.1 | $CH_3$ | 3-$CF_3$ | $CH_3$ | $CH_3$ | $-(CH_2)_2-$ | — |
| 108 | B.1 | $CH_3$ | 3-$CF_3$ | H | H | $-(CH_2)_4-$ | — |
| 110 | B.1 | $CH_3$ | 3-$CF_3$ | $CH_3$ | $C_6H_5CH_2-$ | $-(CH_2)_2-$ | — |

TABLE F.1-continued

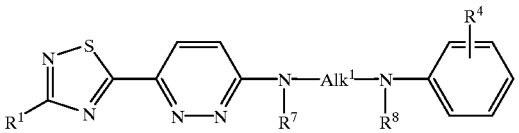

| Co. No. | Ex. No. | R¹ | R⁴ | R⁷ | R⁸ | Alk¹ | Physical data |
|---|---|---|---|---|---|---|---|
| 111 | B.1 | $CH_3$ | 3-$CF_3$ | $CH_3$ | $CH_3$ | —$(CH_2)_4$— | HCl (1:2) |
| 112 | B.1 | $CH_3$ | 3-$CF_3$ | $CH_3$ | H | —$(CH_2)_2$— | — |
| 114 | B.1 | $CH_3$ | 3-$CF_3$ | $CH_3$ | H | —$(CH_2)_4$— | HCl (1:2) |
| 115 | B.1 | $CH_3$ | 3-$CF_3$ | H | $CH_3$ | —$(CH_2)_5$— | — |
| 116 | B.1 | $CH_3$ | 3-$CF_3$ | $CH_3$ | $CH_3$ | —$(CH_2)_5$— | — |
| 117 | B.1 | $CH_3$ | 3-$CF_3$ | H | H | —$(CH_2)_5$— | — |

TABLE F.2

| Co. No. | Ex. No. | R¹ | R⁷ | Alk¹ | R⁴ | R⁵ | Physical data |
|---|---|---|---|---|---|---|---|
| 11 | B.1 | H | H | —$(CH_2)_4$— | 3-$CF_3$ | H | — |
| 12 | B.1 | H | $CH_3$ | —$(CH_2)_4$— | 3-$CF_3$ | H | — |
| 13 | B.1 | $CH_3$ | H | —$(CH_2)_4$— | H | H | mp. 186° C. |
| 14 | B.1 | $CH_3$ | H | —$(CH_2)_4$— | 4-Br | H | — |
| 15 | B.1 | $CH_3$ | H | —$(CH_2)_4$— | 2-Cl | H | — |
| 16 | B.1 | $CH_3$ | H | —$(CH_2)_4$— | 4-Cl | H | — |
| 17 | B.1 | $CH_3$ | H | —$(CH_2)_4$— | 3-Cl | 4-Cl | mp. 181° C. |
| 18 | B.1 | $CH_3$ | H | —$(CH_2)_4$— | 2-Cl | 4-$OCH_3$ | — |
| 19 | B.1 | $CH_3$ | H | —$(CH_2)_4$— | 2-F | H | — |
| 20 | B.1 | $CH_3$ | H | —$(CH_2)_4$— | 3-F | H | — |
| 21 | B.1 | $CH_3$ | H | —$(CH_2)_4$— | 4-F | H | — |
| 22 | B.1 | $CH_3$ | H | —$(CH_2)_4$— | 2-F | 4-F | — |
| 23 | B.1 | $CH_3$ | H | —$(CH_2)_4$— | 3-F | 4-F | — |
| 24 | B.1 | $CH_3$ | H | —$(CH_2)_2$— | 3-$CF_3$ | H | — |
| 25 | B.1 | $CH_3$ | H | —$(CH_2)_3$— | 3-$CF_3$ | H | — |
| 26 | B.1 | $CH_3$ | H | —$(CH_2)_4$— | 3-$CF_3$ | H | — |
| 27 | B.2 | $CH_3$ | H | —$(CH_2)_5$— | 3-$CF_3$ | H | mp. 84–85° C. |
| 28 | B.2 | $CH_3$ | H | —$(CH_2)_6$— | 3-$CF_3$ | H | — |
| 29 | B.1 | $CH_3$ | H | —$(CH_2)_4$— | 2-$CH(CH_3)_2$ | 5-$CH_3$ | — |
| 30 | B.1 | $CH_3$ | H | —$(CH_2)_4$— | 3-$OCH_3$ | H | mp. 152° C. |
| 31 | B.1 | $CH_3$ | H | —$(CH_2)_4$— | 4-$OCH_3$ | H | mp. 172° C. |
| 32 | B.2 | $CH_3$ | H | —$(CH_2)_4$— | 3-$OCH_3$ | 4-$OCH_3$ | — |
| 33 | B.2 | $CH_3$ | H | —$(CH_2)_4$— | —$COOCH_2CH_3$ | H | — |
| 34 | B.1 | $CH_3$ | H | —$(CH_2)_4$— | 3-$NO_2$ | H | mp. 138° C. |
| 35 | B.1 | $CH_3$ | $CH_3$ | —$(CH_2)_4$— | H | H | mp. 106° C. |
| 36 | B.1 | $CH_3$ | $CH_3$ | —$(CH_2)_4$— | 4-Br | H | — |
| 37 | B.1 | $CH_3$ | $CH_3$ | —$(CH_2)_4$— | 2-Cl | H | •HCl (1:1) |
| 38 | B.1 | $CH_3$ | $CH_3$ | —$(CH_2)_4$— | 4-Cl | H | — |
| 39 | B.1 | $CH_3$ | $CH_3$ | —$(CH_2)_4$— | 3-Cl | 4-Cl | — |
| 40 | B.2 | $CH_3$ | $CH_3$ | —$(CH_2)_4$— | 2-Cl | 4-$OCH_3$ | — |
| 41 | B.1 | $CH_3$ | $CH_3$ | —$(CH_2)_4$— | 2-F | H | •HCl (1:1) |
| 42 | B.1 | $CH_3$ | $CH_3$ | —$(CH_2)_4$— | 3-F | H | •HCl (1.1) |
| 43 | B.1 | $CH_3$ | $CH_3$ | —$(CH_2)_4$— | 4-F | H | — |
| 44 | B.1 | $CH_3$ | $CH_3$ | —$(CH_2)_4$— | 2-F | 4-F | •HCl (1:1) |
| 45 | B.1 | $CH_3$ | $CH_3$ | —$(CH_2)_4$— | 3-F | 4-F | — |
| 46 | B.2 | $CH_3$ | $CH_3$ | —$(CH_2)_4$— | 2-F | 3-$CF_3$ | •HCl (1:1) |
| 47 | B.2 | $CH_3$ | $CH_3$ | —$(CH_2)_4$— | 2-F | 5-$CF_3$ | — |
| 48 | B.2 | $CH_3$ | $CH_3$ | —$(CH_2)_4$— | 3-F | 5-$CF_3$ | •HCl (1:1) |
| 49 | B.2 | $CH_3$ | $CH_3$ | —$(CH_2)_4$— | 2-$CF_3$ | H | •HCl (1:1) |
| 50 | B.1 | $CH_3$ | $CH_3$ | —$(CH_2)_2$— | 3-$CF_3$ | H | — |
| 51 | B.1 | $CH_3$ | $CH_3$ | —$(CH_2)_3$— | 3-$CF_3$ | H | •HCl (1:1) |
| 52 | B.1 | $CH_3$ | $CH_3$ | —$(CH_2)_4$— | 3-$CF_3$ | H | — |
| 53 | B.2 | $CH_3$ | $CH_3$ | —$(CH_2)_4$— | 3-$CF_3$ | 5-$CF_3$ | — |
| 54 | B.2 | $CH_3$ | $CH_3$ | —$(CH_2)_4$— | 3-$CF_3$ | 4-$NO_2$ | •HCl (1:1) |
| 55 | B.2 | $CH_3$ | $CH_3$ | —$(CH_2)_4$— | 4-$CF_3$ | H | •HCl (1.1) |
| 56 | B.2 | $CH_3$ | $CH_3$ | —$(CH_2)_4$— | 2-$NO_2$ | 4-Br | — |
| 57 | B.1 | $CH_3$ | $CH_3$ | —$(CH_2)_4$— | 3-$NO_2$ | H | mp.: 133° C. |

TABLE F.2-continued

| Co. No. | Ex. No. | $R^1$ | $R^7$ | Alk$^1$ | $R^4$ | $R^5$ | Physical data |
|---|---|---|---|---|---|---|---|
| 58 | B.1 | CH$_3$ | CH$_3$ | —(CH$_2$)$_4$— | 3-OCH$_3$ | H | •HCl (1:1) |
| 59 | B.1 | CH$_3$ | CH$_3$ | —(CH$_2$)$_4$— | 4-OCH$_3$ | H | mp. 122° C. |
| 60 | B.1 | CH$_3$ | CH$_3$ | —(CH$_2$)$_4$— | 3-OCH$_3$ | 4-OCH$_3$ | mp. 135° C.; •HCl (1:1) |
| 61 | B.1 | CH$_3$ | CH$_3$ | —(CH$_2$)$_4$— | 3-CH$_3$ | H | mp. 121° C.; •HCl (1:1) |
| 62 | B.1 | CH$_3$ | CH$_3$ | —(CH$_2$)$_4$— | 2-CH(CH$_3$)$_2$ | 5-CH$_3$ | — |
| 63 | B.1 | CH$_3$ | CH$_3$CH$_2$— | —(CH$_2$)$_4$— | 3-CF$_3$ | H | — |
| 64 | B.1 | CH$_3$ | CH$_3$(CH$_2$)$_2$— | —(CH$_2$)$_4$— | 3-CF$_3$ | H | — |
| 65 | B.1 | CH$_3$ | CH$_3$(CH$_2$)$_3$— | —(CH$_2$)$_4$— | 3-CF$_3$ | H | — |
| 66 | B.2 | CH$_3$ | C$_6$H$_5$CH$_2$— | —(CH$_2$)$_4$— | 3-CF$_3$ | H | — |
| 67 | B.1 | (CH$_3$)$_2$N— | H | —(CH$_2$)$_4$— | 3-CF$_3$ | H | — |
| 68 | B.1 | (CH$_3$)$_2$N— | CH$_3$ | —(CH$_2$)$_4$— | 3-CF$_3$ | H | •HCl (1:1) |
| 98 | B.1 | H | H | —(CH$_2$)$_2$— | 3-CF$_3$ | H | — |
| 99 | B.1 | H | CH$_3$ | —(CH$_2$)$_2$— | 3-CF$_3$ | H | — |
| 100 | B.1 | (CH$_3$)$_2$N— | CH$_3$ | —(CH$_2$)$_2$— | 3-CF$_3$ | H | — |
| 101 | B.1 | C$_6$H$_5$CH$_2$—OCH$_2$ | CH$_3$ | —(CH$_2$)$_4$— | 3-CF$_3$ | H | — |
| 102 | B.5 | HO—CH$_2$— | CH$_3$ | —(CH$_2$)$_4$ | 3-CF$_3$ | H | HCl |
| 109 | B.1 | CH$_3$ | CH$_3$ | —(CH$_2$)$_4$ | 3-NH$_2$ | H | HCl (1:2); H$_2$O (1:1) |
| 113 | B.1 | CH$_3$ | H | —(CH$_2$)$_4$— | 3-NH$_2$ | H | — |

TABLE F.3

| Co. No. | Ex. No. | $R^7$ | Alk$^1$ | X | $R^4$ | $R^5$ | Physical data |
|---|---|---|---|---|---|---|---|
| 69 | B.3 | H | —(CH$_2$)$_4$— | C=O | 3-CF$_3$ | H | mp. 158° C. |
| 70 | B.3 | CH$_3$ | —(CH$_2$)$_4$— | C=O | 3-CF$_3$ | H | mp. 104° C. |
| 71 | B.1 | H | —(CH$_2$)$_4$— | S | 4-F | H | — |
| 72 | B.1 | CH$_3$ | —(CH$_2$)$_4$— | S | 4-F | H | — |
| 73 | B.1 | H | —(CH$_2$)$_4$— | S | 3-CF$_3$ | H | — |
| 74 | B.1 | CH$_3$ | —(CH$_2$)$_4$— | S | 3-CF$_3$ | H | •HCl (1:1) |
| 75 | B.1 | H | —(CH$_2$)$_5$— | direct bond | 4-F | H | — |
| 76 | B.1 | CH$_3$ | —(CH$_2$)$_5$— | direct bond | 4-F | H | •HCl (1:1) |
| 77 | B.1 | H | —(CH$_2$)$_5$— | direct bond | 3-CF$_3$ | H | mp. 134° C. |
| 78 | B.1 | CH$_3$ | —(CH$_2$)$_5$— | direct bond | 3-CF$_3$ | H | HCl (1:1) |

TABLE F.4

| Co. No. | Ex. No. | $R^7$ | —Alk$^1$—X—Alk$^2$ | $R^4$ |
|---|---|---|---|---|
| 79 | B.1 | H | —(CH$_2$)$_3$—O—CH$_2$*— | 4-F |
| 80 | B.1 | CH$_3$ | —(CH$_2$)$_3$—O—CH$_2$*— | 4-F |

*CH$_2$ moiety is linked with phenyl bearing $R^4$

TABLE F.5
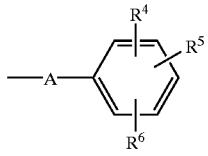
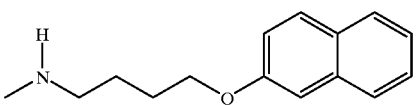
| Co. No. | Ex. No. | | Physical Data |
|---|---|---|---|
| 81 | B.1 | 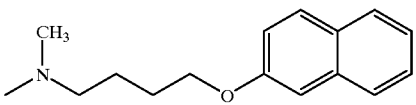 | — |
| 82 | B.1 | 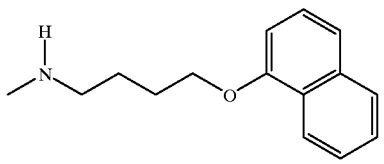 | — |
| 83 | B.1 | 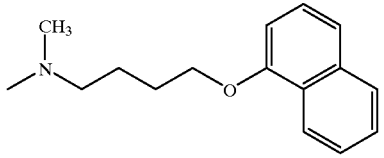 | — |
| 84 | B.1 | 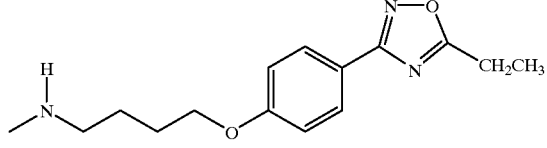 | •HCl (1:1) |
| 85 | B.1 | 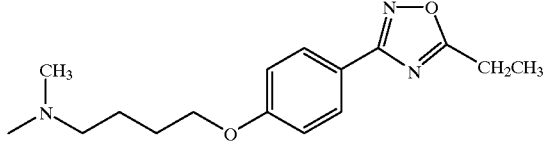 | — |
| 86 | B.1 | 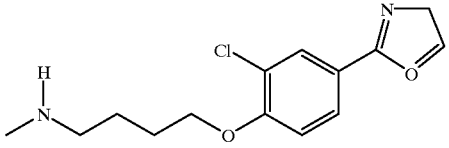 | •HCl (1:1) |
| 87 | B.2 | | — |

TABLE F.5-continued
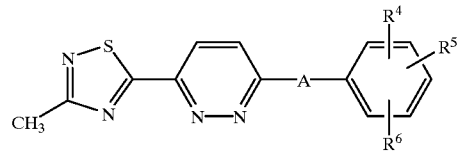
| Co. No. | Ex. No. | | Physical Data |
|---|---|---|---|
| 88 | B.1 | 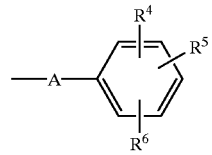 | — |
| 89 | B.1 | 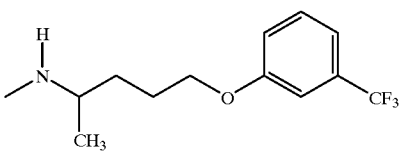 | •HCl (1:1) |
| 90 | B.2 | 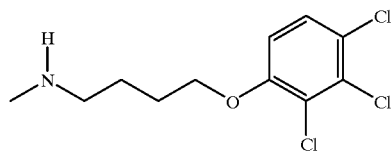 | — |
| 91 | B.1 | 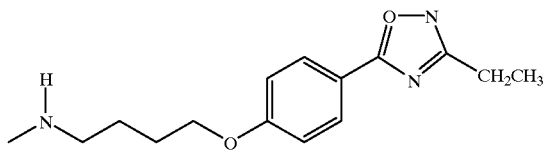 | — |
| 92 | B.1 | 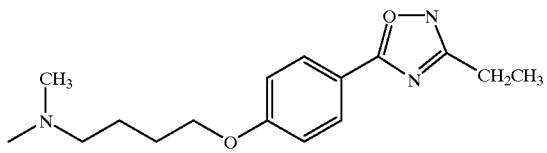 | — |
| 93 | B.2 | 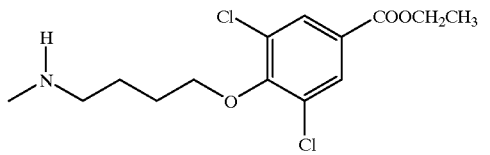 | — |
| 94 | B.4 | 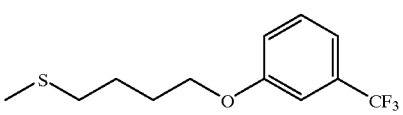 | — |

TABLE F.5-continued
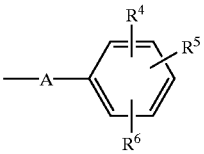
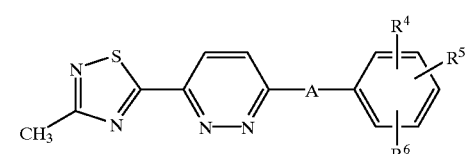
| Co. No. | Ex. No. | | Physical Data |
|---|---|---|---|
| 95 | B.1 | 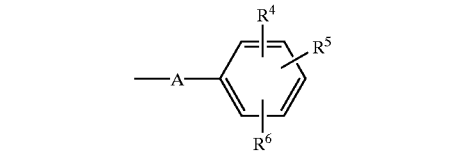 | mp. 136° C. |
| 96 | B.1 | 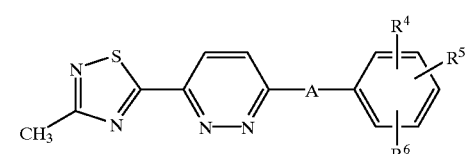 | mp. 82° C. |
| 103 | B.1 | 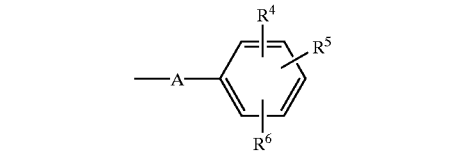 | — |
TABLE F.6
| Co. No. | Carbon Exp. | Theor. | Hydrogen Exp. | Theor. | Nitrogen Exp. | Theor. |
|---|---|---|---|---|---|---|
| 3  | 59.7  | 59.98 | 5.9  | 5.92 | 24.59 | 24.69 |
| 6  | 50.22 | 50.52 | 3.85 | 3.97 | 22.19 | 22.09 |
| 7  | 51.75 | 51.77 | 4.30 | 4.34 | 21.59 | 21.31 |
| 11 | 51.70 | 51.64 | 4.12 | 4.08 | 18.00 | 17.71 |
| 12 | 52.40 | 52.80 | 4.57 | 4.43 | 16.92 | 17.10 |
| 14 | 48.33 | 48.58 | 4.18 | 4.32 | 16.60 | 16.66 |
| 15 | 53.95 | 54.32 | 4.91 | 4.83 | 18.87 | 18.63 |
| 16 | 53.90 | 54.32 | 4.61 | 4.83 | 18.71 | 18.63 |
| 18 | 53.11 | 53.26 | 4.86 | 4.97 | 17.24 | 17.25 |
| 19 | 56.78 | 56.81 | 5.04 | 5.05 | 19.97 | 19.48 |
| 20 | 56.71 | 56.81 | 5.03 | 5.05 | 19.75 | 19.48 |
| 21 | 56.73 | 56.81 | 5.02 | 5.05 | 19.77 | 19.48 |
| 22 | 53.38 | 54.10 | 4.42 | 4.54 | 18.89 | 18.56 |
| 23 | 52.43 | 54.10 | 4.37 | 4.54 | 18.27 | 18.56 |
| 24 | 50.15 | 50.39 | 3.57 | 3.70 | 18.25 | 18.36 |
| 25 | 51.84 | 51.64 | 3.76 | 4.08 | 17.74 | 17.71 |
| 26 | 52.70 | 52.80 | 4.39 | 4.43 | 17.51 | 17.10 |
| 28 | 54.91 | 54.91 | 5.05 | 5.07 | 16.15 | 16.01 |
| 29 | 63.00 | 63.45 | 6.75 | 6.85 | 17.60 | 17.62 |
| 32 | 57.13 | 56.84 | 5.74 | 5.77 | 17.60 | 17.44 |
| 33 | 57.83 | 58.09 | 5.43 | 5.61 | 17.15 | 16.94 |
| 36 | 49.93 | 49.77 | 4.65 | 4.64 | 16.36 | 16.12 |
| 37 | 50.74 | 50.71 | 4.88 | 4.96 | 16.58 | 16.43 |
| 38 | 55.55 | 55.45 | 5.17 | 5.17 | 18.23 | 17.96 |
| 39 | 50.66 | 50.95 | 4.96 | 4.51 | 16.11 | 16.50 |
| 40 | 54.32 | 54.34 | 5.30 | 5.28 | 16.83 | 16.68 |
| 41 | 53.06 | 52.74 | 5.18 | 5.16 | 17.26 | 17.08 |
| 43 | 57.67 | 57.89 | 5.37 | 5.40 | 19.13 | 18.75 |
| 44 | 50.79 | 50.52 | 4.61 | 4.71 | 16.80 | 16.37 |
| 46 | 47.68 | 47.75 | 4.18 | 4.22 | 14.48 | 14.65 |
| 47 | 51.41 | 51.70 | 4.24 | 4.34 | 15.97 | 15.86 |
| 49 | 49.68 | 49.62 | 4.71 | 4.60 | 15.58 | 15.23 |
| 51 | 48.23 | 48.49 | 4.39 | 4.29 | 15.72 | 15.71 |
| 52 | 53.82 | 53.89 | 4.73 | 4.76 | 16.86 | 16.54 |
| 53 | 48.49 | 48.88 | 3.86 | 3.90 | 14.50 | 14.25 |
| 54 | 45.10 | 45.20 | 3.89 | 3.99 | 16.37 | 16.64 |
| 55 | 49.39 | 49.62 | 4.46 | 4.60 | 15.08 | 15.23 |
| 56 | 45.09 | 45.10 | 3.98 | 4.00 | 17.41 | 17.53 |
| 62 | 64.07 | 64.20 | 7.04 | 7.10 | 17.01 | 17.02 |
| 63 | 54.63 | 54.91 | 5.07 | 5.07 | 16.10 | 16.01 |
| 64 | 55.51 | 55.86 | 5.38 | 5.36 | 15.58 | 15.51 |
| 65 | 56.69 | 56.76 | 5.67 | 5.63 | 15.08 | 15.04 |
| 66 | 60.32 | 60.11 | 4.88 | 4.84 | 13.76 | 14.02 |
| 67 | 51.93 | 52.05 | 4.76 | 4.83 | 19.41 | 19.17 |
| 71 | 54.02 | 54.38 | 4.70 | 4.83 | 18.84 | 18.65 |
| 72 | 55.29 | 55.50 | 5.06 | 5.18 | 18.13 | 17.98 |
| 73 | 50.66 | 50.81 | 4.15 | 4.26 | 16.72 | 16.46 |
| 74 | 47.88 | 47.94 | 4.42 | 4.45 | 14.72 | 14.71 |
| 75 | 60.33 | 60.48 | 5.58 | 5.64 | 19.62 | 19.59 |
| 76 | 56.41 | 55.94 | 5.66 | 5.68 | 17.09 | 17.17 |
| 78 | 52.95 | 52.46 | 5.16 | 5.06 | 15.72 | 15.29 |
| 79 | 56.45 | 56.81 | 5.02 | 5.05 | 19.61 | 19.48 |

TABLE F.6-continued

| Co. No. | Carbon Exp. | Carbon Theor. | Hydrogen Exp. | Hydrogen Theor. | Nitrogen Exp. | Nitrogen Theor. |
|---|---|---|---|---|---|---|
| 80 | 57.51 | 57.89 | 5.49 | 5.40 | 19.21 | 18.75 |
| 81 | 64.31 | 64.43 | 5.44 | 5.41 | 18.00 | 17.89 |
| 82 | 64.74 | 65.16 | 5.64 | 5.72 | 17.10 | 17.27 |
| 83 | 64.19 | 64.43 | 5.34 | 5.41 | 18.29 | 17.89 |
| 84 | 59.88 | 59.79 | 5.43 | 5.47 | 16.10 | 15.85 |
| 85 | 57.70 | 57.65 | 5.06 | 5.30 | 22.37 | 22.41 |
| 86 | 55.66 | 54.15 | 5.30 | 5.37 | 20.88 | 20.09 |
| 87 | 53.74 | 53.99 | 4.69 | 4.76 | 19.00 | 18.89 |
| 88 | 53.50 | 53.89 | 4.74 | 4.76 | 16.58 | 16.54 |
| 90 | 45.93 | 45.91 | 3.56 | 3.63 | 15.79 | 15.75 |
| 91 | 57.64 | 57.65 | 5.23 | 5.30 | 22.56 | 22.41 |
| 92 | 58.28 | 58.52 | 5.52 | 5.58 | 21.65 | 21.71 |
| 93 | 49.40 | 49.80 | 4.30 | 4.39 | 14.02 | 14.52 |
| 94 | 50.76 | 50.69 | 4.00 | 4.02 | 13.50 | 13.14 |
| 98 | 48.85 | 49.04 | 3.12 | 3.29 | 19.44 | 19.06 |
| 99 | 50.14 | 50.39 | 3.65 | 3.70 | 18.24 | 18.36 |
| 100 | 50.73 | 50.94 | 4.57 | 4.51 | 19.84 | 19.80 |
| 102 | 48.30 | 47.95 | 4.42 | 4.45 | 14.59 | 14.72 |
| 103 | 53.53 | 53.89 | 4.68 | 4.76 | 16.39 | 16.54 |
| 104 | 52.71 | 52.93 | 4.57 | 4.69 | 20.62 | 20.58 |
| 105 | 52.20 | 51.77 | 4.31 | 4.34 | 21.89 | 21.31 |
| 106 | 53.90 | 54.02 | 4.91 | 5.01 | 19.92 | 19.89 |
| 107 | 51.31 | 52.93 | 4.48 | 4.69 | 19.74 | 20.58 |
| 108 | 52.65 | 52.93 | 4.58 | 4.69 | 20.64 | 20.58 |
| 109 | 47.18 | 46.86 | 5.61 | 5.68 | 17.85 | 18.21 |
| 110 | 59.42 | 59.49 | 4.66 | 4.78 | 17.37 | 17.34 |
| 111 | 47.10 | 47.16 | 5.07 | 4.95 | 16.16 | 16.50 |
| 112 | 51.64 | 51.77 | 4.30 | 4.34 | 21.26 | 21.31 |
| 113 | 57.33 | 57.28 | 5.93 | 5.66 | 23.97 | 23.58 |
| 114 | 47.33 | 46.07 | 4.50 | 4.68 | 17.38 | 16.96 |
| 115 | 55.09 | 55.03 | 5.47 | 5.31 | 19.33 | 19.25 |
| 116 | 49.11 | 48.19 | 5.06 | 5.20 | 16.38 | 16.06 |
| 117 | 54.29 | 54.02 | 4.76 | 5.01 | 19.87 | 19.89 |

C. Pharmacological Examples

EXAMPLE C.1

Angiogenesis inhibitory activity was measured in vitro using the rat aortic ring model of angiogenesis as described by Nicosia, R. F. and Ottinetti in "Laboratory Investigation", vol. 63, p. 115, 1990. The ability of compounds to inhibit microvessel formation was compared to vehicle-treated control rings. Quantitation (microvessel area) following eight days in culture was performed using an image analysis system, consisting of a light microscope, a CCD camera and an automated, custom-designed image analysis program as described by Nissanov, J., Tuman, R. W., Gruver, L. M., and Fortunato, J. M. in "Laboratory Investigation", vol 73 (#5), p. 734, 1995. Compounds were tested at several concentrations for determination of inhibitory potency ($IC_{50}$'s). Several compounds, as listed in table C.1, have an $IC_{50}$ value lower than 100 nM.

TABLE C.1

| Co. No. | $IC_{50}$ |
|---|---|
| 1 | $17.1 \times 10^{-08}$ |
| 3 | $4.57 \times 10^{-08}$ |
| 4 | $2.12 \times 10^{-08}$ |
| 5 | $1.64 \times 10^{-08}$ |
| 6 | $4.28 \times 10^{-10}$ |
| 7 | $4.54 \times 10^{-08}$ |
| 8 | $8.53 \times 10^{-09}$ |
| 9 | $1.79 \times 10^{-08}$ |
| 10 | $1.56 \times 10^{-08}$ |
| 11 | $9.08 \times 10^{-08}$ |

TABLE C.1-continued

| Co. No. | $IC_{50}$ |
|---|---|
| 14 | $3.12 \times 10^{-08}$ |
| 15 | $1.34 \times 10^{-09}$ |
| 16 | $1.58 \times 10^{-08}$ |
| 17 | $1.28 \times 10^{-08}$ |
| 20 | $8.15 \times 10^{-09}$ |
| 21 | $4.84 \times 10^{-08}$ |
| 22 | $7.26 \times 10^{-08}$ |
| 24 | $1.33 \times 10^{-09}$ |
| 25 | $4.04 \times 10^{-08}$ |
| 26 | $3.97 \times 10^{-09}$ |
| 27 | $6.22 \times 10^{-10}$ |
| 28 | $1.76 \times 10^{-09}$ |
| 29 | $2.48 \times 10^{-08}$ |
| 30 | $6.31 \times 10^{-09}$ |
| 35 | $2.94 \times 10^{-08}$ |
| 36 | $5.30 \times 10^{-09}$ |
| 37 | $1.32 \times 10^{-09}$ |
| 38 | $3.72 \times 10^{-08}$ |
| 39 | $1.71 \times 10^{-08}$ |
| 40 | $1.15 \times 10^{-08}$ |
| 41 | $2.56 \times 10^{-08}$ |
| 42 | $4.22 \times 10^{-08}$ |
| 43 | $2.78 \times 10^{-09}$ |
| 44 | $1.52 \times 10^{-08}$ |
| 45 | $2.00 \times 10^{-09}$ |
| 46 | $1.46 \times 10^{-09}$ |
| 47 | $1.25 \times 10^{-08}$ |
| 48 | $1.85 \times 10^{-09}$ |
| 49 | $3.12 \times 10^{-10}$ |
| 50 | $8.30 \times 10^{-10}$ |
| 51 | $9.38 \times 10^{-09}$ |
| 52 | $5.56 \times 10^{-09}$ |
| 53 | $7.33 \times 10^{-09}$ |
| 54 | $1.37 \times 10^{-08}$ |
| 55 | $3.62 \times 10^{-09}$ |
| 56 | $8.07 \times 10^{-08}$ |
| 57 | $5.11 \times 10^{-08}$ |
| 61 | $3.51 \times 10^{-08}$ |
| 62 | $5.53 \times 10^{-09}$ |
| 63 | $9.20 \times 10^{-09}$ |
| 67 | $3.24 \times 10^{-08}$ |
| 70 | $1.22 \times 10^{-08}$ |
| 71 | $<1.00 \times 10^{-10}$ |
| 72 | $3.88 \times 10^{-10}$ |
| 73 | $2.86 \times 10^{-09}$ |
| 74 | $1.00 \times 10^{-09}$ |
| 76 | $1.15 \times 10^{-09}$ |
| 77 | $5.81 \times 10^{-09}$ |
| 78 | $2.80 \times 10^{-10}$ |
| 82 | $6.71 \times 10^{-08}$ |
| 84 | $1.74 \times 10^{-08}$ |
| 86 | $6.90 \times 10^{-09}$ |
| 89 | $2.06 \times 10^{-09}$ |
| 94 | $4.71 \times 10^{-09}$ |
| 95 | $7.03 \times 10^{-10}$ |
| 96 | $5.08 \times 10^{-10}$ |
| 97 | $1.60 \times 10^{-09}$ |
| 98 | $3.07 \times 10^{-09}$ |
| 100 | $7.01 \times 10^{-09}$ |
| 102 | $2.08 \times 10^{-09}$ |
| 103 | $8.04 \times 10^{-09}$ |
| 104 | $2.03 \times 10^{-08}$ |
| 105 | $1.49 \times 10^{-09}$ |
| 108 | $3.79 \times 10^{-08}$ |
| 110 | $6.98 \times 10^{-09}$ |
| 111 | $1.87 \times 10^{-09}$ |
| 112 | $1.33 \times 10^{-08}$ |

What is claimed is:

1. A method of inhibiting abnormal angiogenesis in a subject having a disease or disorder associated with abnormal angiogenesis, said disease or disorder selected from the group consisting of solid tumor growth, ocular neovascular diseases, neovascular glaucoma, diabetic retinopathy, retrolental fibroplasia, hemangiomas, angiofibromas, psoriasis, osteoarthritis, and rheumatoid arthritis, comprising administering to said subject an effective amount of a compound of formula (I),

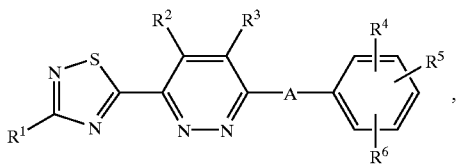

the N-oxide forms, the pharmaceutically acceptable acid addition salts and stereochemically isomeric forms thereof, wherein $R^1$ is hydrogen, $C_{1-6}$alkyl, $C_{1-6}$alkyloxy, $C_{1-6}$alkylthio, amino, mono- or di($C_{1-6}$alkyl)amino, $Ar^1$, $Ar^1$—NH—, $C_{3-6}$cycloalkyl, hydroxymethyl or benzyloxymethyl;

$R^2$ and $R^3$ are hydrogen, or taken together may form a bivalent radical of formula —CH=CH—CH=CH—;

$R^4$, $R^5$ and $R^6$ are each independently selected from hydrogen, halo, $C_{1-6}$alkyl, $C_{1-6}$alkyloxy, trifluoromethyl, nitro, amino, cyano, azido, $C_{1-6}$alkyloxy$C_{1-6}$alkyl, $C_{1-6}$alkylthio, $C_{1-6}$alkyloxycarbonyl or $Het^1$;

or when $R^4$ and $R^5$ are adjacent to each other they may be taken together to form a radical of formula —CH=CH—CH=CH—;

A is a bivalent radical of formula

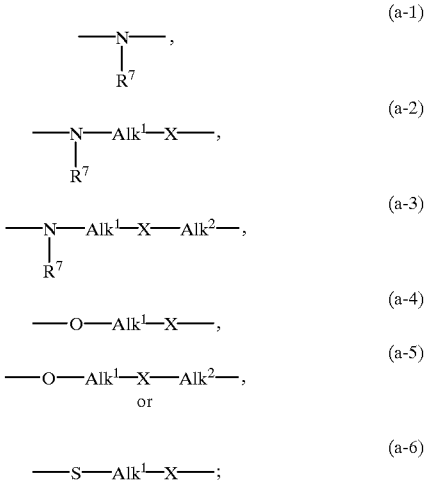

wherein X is a direct bond, —O—, —S—, C=O, —NR$^8$— or $Het^2$;

$R^7$ is hydrogen, $C_{1-6}$alkyl or $Ar^2$methyl;
$R^8$ is hydrogen, $C_{1-6}$alkyl or $Ar^2$ methyl;
$Alk^1$ is $C_{1-6}$alkanediyl;
$Alk^2$ is $C_{1-4}$alkanediyl;
$Ar^1$ is phenyl; phenyl substituted with 1, 2, or 3 substituents each independently selected from halo, $C_{1-6}$alkyl, $C_{1-6}$alkyloxy, trihalomethyl, amino or nitro;
$Ar^2$ is phenyl; phenyl substituted with 1, 2 or 3 substituents each independently selected from halo, $C_{1-6}$alkyl, $C_{1-6}$alkyloxy, trihalomethyl, amino or nitro;
$Het^1$ is a monocyclic heterocycle selected from oxazolyl, isoxazolyl, oxadiazolyl, thiazolyl, isothiazolyl, thiadiazolyl or oxazolinyl; and each monocyclic heterocycle may optionally be substituted on a carbon atom with $C_{1-4}$alkyl; and $Het^2$ is tetrahydrofuran; a tetrahydrofuran substituted with $C_{1-6}$alkyl; a dioxane; a dioxane substituted with $C_{1-6}$alkyl; a dioxolane; or a dioxolane substituted with $C_{1-6}$alkyl;

wherein said effective amount comprises from 0.001 mg/kg to 10 mg/kg body weight.

2. The method of claim 1, wherein in the compound of formula I $R^1$ is hydrogen, $C_{1-6}$alkyl or di($C_{1-6}$alkyl)amino; $R^2$ and $R^3$ are hydrogen; $R^4$, $R^5$ and $R^6$ are each independently selected from hydrogen, halo, $C_{1-4}$alkyl, $C_{1-4}$alkyloxy, trifluoromethyl, nitro, $C_{1-6}$alkyloxycarbonyl or $Het^1$; and the bivalent radical A is (a-2), (a-3), (a-4) or (a-6).

3. The method of claim 1, wherein in the compound of formula I the bivalent radical A is (a-2), (a-4), or (a-6) wherein $Alk^1$ is $C_{2-4}$alkanediyl.

4. The method of claim 1, wherein in the compound of formula I $Alk^1$ is butanediyl.

5. The method of claim 1, wherein the compound of formula I is 6-(3-methyl-1,2,4-thiadiazol-5-yl)-N-[4-[3-(trifluoromethyl)phenoxy]butyl-3-pyridazinamine, N-methyl-6-3-1,2,4-thiadiazol-5-yl)-N-[4-[3-(trifluoromethyl)phenoxy]butyl-3-pyridazinamine, or 6-(3-methyl-1,2,4-thiadiazol-5-yl)-N-[4-[3-(trifluoromethyl)phenylthio]butyl-3-pyridazinamine; a stereoisomeric form or a pharmaceutically acceptable acid addition salt thereof.

6. A method of controlling solid tumor growth comprising administering to a host in need thereof an effective amount of a compound of formula I

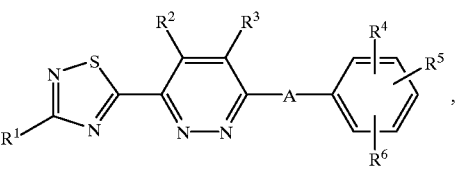

the N-oxide forms, the pharmaceutically acceptable acid addition salts and stereochemically isomeric forms thereof, wherein $R^1$ is hydrogen, $C_{1-6}$alkyl, $C_{1-6}$alkyloxy, $C_{1-6}$alkylthio, amino, mono- or di($C_{1-6}$alkyl)amino, $Ar^1$, $Ar^1$—NH—, $C_{3-6}$cycloalkyl, hydroxymethyl or benzyloxymethyl;

$R^2$ and $R^3$ are hydrogen, or taken together may form a bivalent radical of formula —CH=CH—CH=CH—;

$R^4$, $R^5$ and $R^6$ are each independently selected from hydrogen, halo, $C_{1-6}$alkyl, $C_{1-6}$alkyloxy, trifluoromethyl, nitro, amino, cyano, azido, $C_{1-6}$alkyloxy$C_{1-6}$alkyl, $C_{1-6}$alkylthio, $C_{1-6}$alkyloxycarbonyl or $Het^1$;

or when $R^4$ and $R^5$ are adjacent to each other they may be taken together to form a radical of formula —CH=CH—CH=CH—;

A is a bivalent radical of formula

-continued

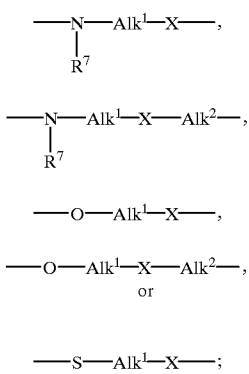

wherein X is a direct bond, —O—, —S—, C=O, —NR$^8$— or Het$^2$;
R$^7$ is hydrogen, C$_{1-6}$alkyl or Ar$^2$methyl;
R$^8$ is hydrogen, C$_{1-6}$alkanediyl;
Alk$^1$ is C$_{1-4}$alkanediyl;
Ar$^1$ is phenyl; phenyl substituted with 1, 2 or 3 substituents each independently selected from halo, C$_{1-6}$alkyl, C$_{1-6}$alkyloxy, trihalomethyl, amino or nitro;
Ar$^2$ is phenyl; phenyl substituted with 1, 2 or 3 substituents each independently selected from halo, C$_{1-6}$alkyl, C$_{1-6}$alkyloxy, trihalomethyl, amino or nitro;
Het$^1$ is a monocyclic heterocycle selected from oxazolyl, isoxazolyl, oxadiazolyl, thiazolyl, isothiazolyl, thiadiazolyl or oxazolinyl; and each monocyclic heterocycle may optionally be substituted on a carbon atom with C$_{1-4}$alkyl; and
Het$^2$ is tetrahydrofuran; a tetrahydrofuran substituted with C$_{1-6}$alkyl; a dioxolane; a dioxolane substituted with C$_{1-6}$alkyl.

7. The method of claim 6, wherein in the compound of formula I R$^1$ is hydrogen, C$_{1-6}$alkyl or di(C$_{1-6}$alkyl)amino; R$^2$ and R$^3$ are hydrogen; R$^4$, R$^5$ and R$^6$ are each independently selected from hydrogen, halo, C$_{1-4}$alkyl, C$_{1-4}$alkyloxy, trifluoromethyl, nitro, C$_{1-6}$alkyloxycarbonyl or Het$^1$; and the bivalent radical A is (a-2), (a-3), (a-4) or (a-6).

8. The method of claim 6, wherein in the compound of formula I the bivalent radical A is (a2), (a-4), or (a-6) wherein Alk$^1$ is C$_{2-4}$alkanediyl.

9. The method of claim 6, wherein in the compound of formula I Alk$^1$ is butanediyl.

10. The method of claim 6, wherein the compound of formula I is 6-(3-methyl-1,2,4-thiadiazol-5-yl)-N-[4-[3-(trifluoromethyl)phenoxy]butyl-3-pyridazinamine, N-methyl-6-(3-methyl-1,2,4-thiadiazol-5-yl)-N-[4-[3-(trifluoromethyl)phenoxy]butyl-3-pyridazinamine, or 6-(3-methyl-1,2,4-thiadiazol-5-yl)-N-[4-[3-(trifluoromethyl)phenylthio]butyl-3-pyridazinamine; a stereoisomeric form or a pharmaceutically acceptable acid addition salt thereof.

* * * * *